United States Patent [19]

Nishimura et al.

[11] Patent Number: 4,528,186
[45] Date of Patent: Jul. 9, 1985

[54] METHOD OF PRODUCING HUMAN EPIDERMAL GROWTH FACTOR

[75] Inventors: Toyohiko Nishimura, Ashiya; Naomi Uchida, Takarazuka; Hajime Hiratani, Sennan, all of Japan

[73] Assignee: Japan Chemical Research Co., Ltd., Kobe, Japan

[21] Appl. No.: 502,661

[22] Filed: Jun. 9, 1983

[30] Foreign Application Priority Data

Jun. 15, 1982 [JP] Japan .................. 57-103292

[51] Int. Cl.$^3$ .................. A61K 35/22; A61K 37/02
[52] U.S. Cl. .................. 424/99; 424/100; 514/2
[58] Field of Search .................. 424/99, 100, 177

[56] References Cited

FOREIGN PATENT DOCUMENTS

| 5167229 | 12/1980 | Japan | 424/95 |
| 6025112 | 3/1981 | Japan | 424/100 |
| 537681 | 5/1975 | U.S.S.R. | 424/99 |

OTHER PUBLICATIONS

Chem. Abstracts, vol. 84, 1976, 84:27148a, Gregory, et al., Isolation of the Urogastrones . . . .
Chem. Abstracts, vol. 91, 1593m, Hirata, et al., "Epidermal Growth Factor (Urogastrone) in Human Fluids . . . ".

*Primary Examiner*—Donald B. Moyer
*Assistant Examiner*—Jacqueline M. Stone
*Attorney, Agent, or Firm*—Burgess, Ryan & Wayne

[57] ABSTRACT

A method for producing a human epidermal growth factor in high yield and high purity by adding particles of an aluminum or magnesium silicate of the formula z.2 (or 6) $SiO_2.xH_2O$ where Z is $Al_2O_3$ or $2MgO$ and x is the number of water molecules in each molecule of the compound, to human urine under neutral to acid conditions to adsorb the factor on the particles and then eluting the factor with an alkaline solution.

8 Claims, No Drawings

METHOD OF PRODUCING HUMAN EPIDERMAL GROWTH FACTOR

This invention relates to a method for producing a human epidermal growth factor.

It is known that a human epidermal growth factor is contained in human urine. This substance is a linear polypeptide with a molecular weight of about 6,000 and 3 sets of disulfide cross-links between molecules, bearing a close resemblance with mouse epidermal growth factor as obtained from the mouse submandibular gland in chemical structure and in physiological activity. This compound has such properties as gastric acid secretion inhibiting activity, epidermal growth promoting activity, etc. and is, therefore, of value as a medicine.

There are known a few methods for recovering the epidermal growth factor from human urine; i.e. the tannic acid precipitation method [H. Gregory et al.: Hoppe-Seyler's Z. Physiol. Chem. 356, 1765 (1975)] and the benzoic acid-acetone powder method [S. Cohen et al.: Proc. Natl. Acad. Sci., U.S.A. 72, 1317 (1975)], but these methods have the disadvantages that human epidermal growth factor cannot be selectively adsorbed and, therefore, the subsequent procedure is complicated and time-consuming and that a large quantity of organic solvent is required.

The present inventors conducted an extensive research for developing a method which would be free from the disadvantages of the conventional methods and with which the desired factor could be easily isolated at low cost by a mass treatment of urine.

As a result, it was discovered that human epidermal growth factor is selectively adsorbed on adsorbents having the formulas $Al_2O_3.2SiO_2.2H_2O$, $Al_2O_3.6SiO_2.2H_2O$ and $2MgO.6SiO_2.xH_2O$ but is not adsorbed at all on adsorbents of the formulas $Al_2O_3.9SiO_2.xH_2O$, $ySiO_2.xH_2O$ and $Al(OH)_3$.

The pertinent experimental data are given in Table 1. The adsorbents were those selected in consideration of practical utility, i.e. low cost, availability, regeneratability, suitability for the treatment of large volumes of urine, and compatibility with both a batch process and a column process.

In the experiment, human epidermal growth factor was adsorbed from human urine on various adsorbents under various pH and eluted with 1N-aqueous ammonia and the rate of recovery of human epidermal growth factor from urine and the purity thereof were investigated.

TABLE 1

| No. | Adsorbent Composition | pH | Yield (%) | Purity (%)/protein |
|---|---|---|---|---|
| 1 | $Al_2O_3.6SiO_2.H_2O$ (Nikkanite ®) | 3 | >99 | 0.18 |
|   |   | 5 | >99 | 0.23 |
|   |   | 7 | 96 | 0.26 |
| 2 | $Al_2O_3.2SiO_2.2H_2O$ (Kaolin) | 3 | >99 | 0.19 |
|   |   | 5 | >94 | 0.25 |
|   |   | 7 | 76 | 0.23 |
| 3 | $Al_2O_3.ySiO_2.xH_2O$ (Granular synthetic zeolite) | 3 | 32 | 0.006 |
|   |   | 5 | 26 | 0.004 |
|   |   | 7 | 25 | 0.004 |
| 4 | $Al(OH)_3$ (Aluminum hydroxide gel) | 3 | 0 | 0 |
|   |   | 5 | 0 | 0 |
|   |   | 7 | 0 | 0 |
| 5 | MgO (KW-100) | 3 | 42 | 0.009 |
|   |   | 5 | 49 | 0.013 |
|   |   | 7 | 24 | 0.003 |
| 6 | $Al_2O_3.xH_2O$ (KW-200) | 3 | 44 | 0.019 |
|   |   | 5 | 43 | 0.016 |
|   |   | 7 | 4 | <0.001 |
| 7 | $2.5MgO.Al_2O_3.xH_2O$ (KW-300) | 3 | 66 | 0.058 |
|   |   | 5 | 28 | 0.033 |
|   |   | 7 | 0 | 0 |
| 8 | $Al(OH)_3.NaHCO_3$ (KW-400) | 3 | 12 | 0.008 |
|   |   | 5 | 26 | 0.032 |
|   |   | 7 | 14 | 0.028 |
| 9 | $Mg_6Al_2(OH)_{16}CO_3.4H_2O$ (KW-500) | 3 | 53 | 0.042 |
|   |   | 5 | 3 | <0.001 |
|   |   | 7 | 0 | 0 |
| 10 | $2MgO.6SiO_2.xH_2O$ (KW-600) | 3 | 95 | 0.25 |
|   |   | 5 | 95 | 0.25 |
|   |   | 7 | 32 | 0.07 |
| 11 | $Al_2O_3.9SiO_2.xH_2O$ (KW-700) | 3 | 26 | 0.004 |
|   |   | 5 | 0 | 0 |
|   |   | 7 | 0 | 0 |
| 12 | $ySiO_2.xH_2O$ Diatomaceus earth | 3 | 0 | 0 |
|   |   | 5 | 0 | 0 |
|   |   | 7 | 0 | 0 |
| Control | Tannic acid adsorption |  | 72 | 0.12 |
|   | Benzoic acid-acetone powder |  | 58 | 0.085 |

[Note]
In the table, adsorbent No. 1 is a product of Nippon Kassei Hakudo K. K.; adsorbents No. 2, No. 3 and No. 12 are products of Wako Pure Chemical Co., Ltd.; and adsorbents No. 4 through No. 11 are products of Kyowa Chemical Industries, Ltd. KW is an abbreviation of KYOWAAD ®.

As will be apparent from Table 1, the use of adsorbents No. 1 ($Al_2O_3.6SiO_2.H_2O$), No. 2 ($Al_2O_3.2SiO_2.2H_2O$) and No. 10 ($2MgO.6SiO_2.xH_2O$) is superior to the conventional tannic acid adsorption and benzoic acid-acetone powder techniques in recovery rate and purity.

On the other hand, human epidermal growth factor is substantially not adsorbed on adsorbents No. 4 ($Al(OH)_3$), No. 11 ($Al_2O_3.9SiO_2.xH_2O$) and No. 12 ($ySiO_2.xH_2O$).

Urine contains a variety of physiologically active substances such as plasminogen activator, uropepsin and other proteases, and the urine of a pregnant woman contains placental gonadotropic hormone as well. These physiologically active substances should not be contained in the product human epidermal growth factor.

In this sense, the relative contents of said physiologically active substances were investigated in the cases where urine was pretreated with the above-mentioned adsorbents No. 4, No. 11 and No. 12 which do not adsorb human epidermal growth factor at all versus the cases where urine was not pretreated.

As test urines, both normal human urine and urine from pregnant women were employed.

As the pretreatment urine samples were contacted with the above-mentioned 3 different adsorbents for a predetermined time and, then, each adsorbent was removed. To the resultant pretreated urine was added one of the abovementioned adsorbents No. 1, No. 2 and No. 10 and the adsorbent was separated, followed by elution with 1N-aqueous ammonia. Using the resultant eluate, the yield and purity of human epidermal growth factor, protease activity and human placental gonadotropic hormone activity were investigated. The results are shown in Table 2 A and B.

TABLE 2A

| (normal human urine) | | | | |
|---|---|---|---|---|
| Adsorbent for pretreatment | Adsorbent | Yield (%) | Purity (%)/protein | Proteinase activity |
| No. 11 | No. 2 | 93 | 0.38 | — |
|  | No. 1 | >99 | 0.43 | — |
|  | No. 10 | 95 | 0.42 | — |

TABLE 2A-continued

| | (normal human urine) | | | |
|---|---|---|---|---|
| Adsorbent for pretreatment | Adsorbent | Yield (%) | Purity (%) /protein | Proteinase activity |
| No. 12 | No. 2 | 93 | 0.36 | — |
| | No. 1 | >99 | 0.38 | — |
| | No. 10 | 95 | 0.40 | — |
| No. 4 | No. 2 | 93 | 0.35 | — |
| | No. 1 | >99 | 0.36 | — |
| | No. 10 | 95 | 0.38 | — |
| Untreated | No. 2 | 94 | 0.25 | ± |
| | No. 1 | >99 | 0.23 | ± |
| | No. 10 | 95 | 0.25 | ± |

TABLE 2B

| | (pregnant women's urine) | | | | |
|---|---|---|---|---|---|
| Adsorbent for pretreatment | Adsorbent | Yield (%) | Purity (%) /protein | Proteinase activity | hCG* activity |
| No. 11 | No. 2 | 92 | 0.42 | — | 0 |
| | No. 1 | >99 | 0.44 | — | 0 |
| | No. 10 | 94 | 0.41 | — | 0 |
| No. 12 | No. 2 | 93 | 0.38 | — | 100 |
| | No. 1 | >99 | 0.39 | — | 100 |
| | No. 10 | 93 | 0.41 | — | 25 |
| No. 4 | No. 2 | 91 | 0.37 | — | 150 |
| | No. 1 | >99 | 0.37 | — | 150 |
| | No. 10 | >94 | 0.38 | — | 50 |
| Untreated | No. 2 | 90 | 0.20 | ± | 1000 |
| | No. 1 | >99 | 0.19 | ± | 1000 |
| | No. 10 | 91 | 0.20 | ± | 500 |

*Human placental gonadotropic hormone IU/mg (protein)

It will be apparent from Table 2 A and B that compared with the control (not pretreated) cases, pretreatment with any of adsorbents No. 11 ($Al_2O_3.9SiO_2.xH_2O$), No. 12 ($SiO_2$) and No. 4 ($Al(OH)_3$) results in an almost doubling increase of purity substantially without a change of product yield and renders protease activity negative.

It is also apparent from Table 2 B that where the material is pregnant women's urine, adsorbent No. 11 ($Al_2O_3.9SiO_2.xH_2O$) is very effective in removing human placental gonadotropic hormone.

This invention is predicated on the above findings. Thus, this invention relates to a method for producing a human epidermal growth factor which comprises adding particles of an aluminium or magnesium silicate of the formula $$Z.2(or\ 6)SiO_2.xH_2O$$

(wherein Z is $Al_2O_3$ or $2MgO$; x is the number of water molecules in each molecule of the compound as governed by the water content of the compound) to human urine under neutral to acidic conditions to thereby adsorb the active factor in the urine on said particles and, then, eluting said active factor with an alkaline solution.

While urine as such may be used in the practice of this invention, it is preferable to pre-adjust urine to pH 8 to 9, preferably pH 8.5, so as to precipitate impurities such as mucopolysaccharides and remove the impurities by a suitable procedure such as filtration.

The adsorbents used for adsorbing the human epidermal growth factor contained in urine are represented by the formula $Al_2O_3.2(or\ 6)SiO_2.xH_2O$ or $2MgO.6SiO_2.xH_2O$. As examples of the former may be mentioned aluminosilicates of the formula $Al_2O_3.6SiO_3.2H_2O$ (adsorbent No. 1 in Table 1) and the formula $Al_2O_3.2SiO_2.2H_2O$ (adsorbent No. 2 in Table 1). As examples of the latter may be mentioned magnesium silicates of the formula $2MgO.6SiO_2.xH_2O$ (adsorbent No. 10 in Table 1).

These adsorbents are added to urine under neutral to acidic conditions. When the adsorbent is an aluminium-silicate as defined hereinbefore, the preferred pH range is 5 to 7. At any pH below 5, impurities tend to be adsorbed. Moreover, when the average particle diameter of said aluminiumsilicate is several tens of meshes, the contact thereof with urine is preferably effected batchwise. For practical purposes, it is preferable to contact 2.5 to 5 grams of the adsorbent with each 1 liter of urine, although the ratio of the adsorbent to urine and the contact time are not limited to these specific figures.

When the adsorbent is the above-mentioned magnesium silicate, the particle diameter of the adsorbent is not especially critical insofar as the object of this invention can be accomplished. However, there are preferable ranges according to the adsorption processes. Thus, for example, the particle size range of 100 to 200 mesh is desirable for a batch process, while the range of 50 to 100 mesh is desirable for columnwise adsorption. Moreover, the adsorbent is preferably added to urine under acidic conditions, preferably at pH 2 to 3. At pH values over 3, the adsorption of human epidermal growth factor tends to be inhibited. While the amount of the adsorbent is not especially critical, it is practically desirable to employ 5 to 10 grams for each 1 liter of urine.

The adsorbent on which the desired factor has been adsorbed is for example, allowed to settle and separated from the supernatant fluid. The factor is then eluted with an alkaline solution, preferably at pH 10 to 12. This solution may for example be 1 to 12N-aqueous ammonia or a 1 to 2N-aqueous solution of sodium carbonate. To concentrate the factor in the eluate, there may be employed any of the various processes such as the process comprising adding a water-miscible organic solvent such as acetone or a salt such as ammonium sulfate to the eluate to thereby precipitate the factor or the process in which water is removed from the eluate by freeze-drying or vacuum distillation. However, for a mass treatment of urine, the salting-out process comprising addition of ammonium sulfate is desirable.

Human urine which is employed in the practice of this invention may be one which has been preliminarily purified with a certain adsorbent so as to remove impurities.

An example of such adsorbent is an aluminiumsilicate of the formula $Al_2O_3.9SiO_2.xH_2O$ (wherein x is as defined hereinbefore), which is available under the tradename of KYOWAAD ®700 (Kyowa Chemical Industries, Ltd.) This can be used for adsorbing impurities in the urine by whichever of a batch process and a columnwise process. The adsorption is preferably conducted under weakly acidic conditions, preferably at pH 3 to 5. At pH levels over 5, the efficiency of adsorption of impurities tends to be reduced. The preferred particle diameter of the adsorbent is 50 to 200 mesh, although sizes outside the above range may be used only if the adsorbent is particulate. The amount of the adsorbent is not especially critical but the range of 5 to 10 g per liter of urine is preferred. The time of contact with urine is generally about 2 hours at the maximum.

Other examples of the adsorbent used for adsorbing impurities are those materials which are generally represented by the formula $ySiO_2.xH_2O$, such as diatomaceus earth, silica gel, etc. Here, adsorption is effected under weakly acidic conditions, preferably at pH 4 to 6. The adsorption procedure, preferred particle size, amount, contact time, etc. with these adsorbent are the same as those stated for the aluminosilicate.

For the adsorption of impurities, aluminum hydroxide is also employed. This material is generally represented by the formula $Al(OH)_3$. Here, adsorption is preferably conducted under substantially neutral conditions and the preferred amount of the adsorbent is 2.5 to 5 grams per liter of urine. The adsorption procedure, preferred particle size, and contact time are the same as those stated for said aluminiumsilicate.

When normal human urine is employed as a raw material for the production of human epidermal growth factor, any of the above-mentioned aluminiumsilicate, silicic acid and aluminum hydroxide can be used as an adsorbent for adsorbing and removing impurities preliminarily from the urine. When pregnant women's urine is employed as a raw material, these adsorbents may similarly be employed but the aluminiumsilicate is particularly useful.

It should, of course, be understood that the combinations of adsorbents for such pretreatment and said adsorption of human epidermal growth factor are not limited to those shown in working examples which appear below but may be selected as may be found suited.

The following examples are further illustrative of this invention.

EXAMPLE 1

One liter of normal human urine was adjusted to pH 8.5 with a 4N-aqueous solution of sodium hydroxide and the resultant precipitate was filtered off. The filtrate was adjusted to pH 3.0 with 6N-HCl and contacted with 10 grams of synthetic magnesium silicate $2MgO.6SiO_2.xH_2O$ (adsorbent No. 10 in Table 1) for 2 hours. The mixture was allowed to stand and the supernatant was separated from the adsorbent. The adsorbent was washed with 10 ml of water and elution was carried out with 20 ml of 1N-aqueous ammonium. The eluate was adjusted to pH 5.6 and ammonia sulfate was added to 50% saturation, whereby human epidermal growth factor was precipitated. The yield of human epidermal growth factor was 28.5 $\mu$g, the purity thereof relative to total protein was 0.25%, and the percent yield was 95%.

EXAMPLE 2

One liter of normal human urine was adjusted to pH 8.5 with 4N-sodium hydroxide and the resulted precipitate was filtered off. The filtrate was adjusted to pH 6.0 with 6N-HCl and contacted with 5 grams of kaolin (adsorbent No. 2 in Table 1) for 2 hours. The mixture was allowed to stand and the supernatant was separated from the adsorbent. The adsorbent was washed with 10 ml of water and elution was carried out with 20 ml of 1N-aqueous ammonia. The eluate was made neutral, and ammonium sulfate was added to 50% saturation, whereby human epidermal growth factor was obtained. 27.7 $\mu$g; purity based on total protein 0.25%; and yield 99%.

EXAMPLE 3

One liter of normal human urine was adjusted to pH 8.5 with 4N-NaOH and the resultant precipitate was filtered off. The filtrate was adjusted to pH 6.5 with 6N-HCl and contacted with 5 grams of synthetic aluminiumsilicate $Al_2O_3.6SiO_2.H_2O$ (adsorbent No. 1 in Table 1) for 1 hour. The mixture was allowed to stand and the supernatant was separated from the adsorbent. The adsorbent was washed with 10 ml of water and elution was carried out with 20 ml of 1N-aqueous ammonia. After the eluate was made neutral, ammonium sulfate was added to 50% saturation, whereby human epidermal growth factor was precipitated. The amount of human epidermal growth factor was 29.4 $\mu$g; purity based on total protein 0.23%; and recovery rate 99%.

EXAMPLE 4

One liter of normal human urine was adjusted to pH 8.5 with 4N-NaOH and the resultant precipitate was filtered off. The filtrate was adjusted to pH 7.0 with 6N-HCl and contacted with 5 grams of aluminum hydroxide powder for 2 hrs. The mixture was allowed to stand and the supernatant was separated from the adsorbent. The supernatant was adjusted to pH 3.0 with 6N-HCl and contacted with 10 grams of the same synthetic magnesium silicate $2MgO.6SiO_2.xH_2O$ (KYO-WAAD® 600) as used in Example 1 for 2 hrs. The mixture was allowed to stand and the supernatant was separated from the absorbent. The adsorbent was washed with 10 ml of water and elution was carried out with 20 ml of 1N-aqueous ammonia. After the eluate was adjusted to pH 5.6, ammonium sulfate was added to 50% saturation, whereby human epidermal growth factor was precipitated. The amount of human epidermal growth factor thus obtained was 26.8 $\mu$g, the purity thereof based on total protein was 0.43%, and the rate of recovery was 93%.

EXAMPLE 5

One liter of urine from pregnant women was adjusted to pH 8.5 with 4N-NaOH and the resultant precipitate was filtered off. The filtrate was adjusted to pH 4.5 with 6N-HCl and contacted with 10 grams of synthetic aluminiumsilicate $Al_2O_3.9SiO_2.xH_2O$ (adsorbent No. 11 in Table 1) for 2 hrs. The mixture was allowed to stand and the supernatant was separated from the adsorbent. To the supernatant was added 5 grams of synthetic aluminiumsilicate $Al_2O_3.6SiO_2.H_2O$ (adsorbent No. 1 in Table 1) and the mixture was stirred for 2 hrs. The mixture was allowed to stand and the supernatant was separated from the adsorbent. The adsorbent was washed with 10 ml of water and elution was carried out with 20 ml of 1N-aqueous ammonia. The eluate was made neutral and ammonium sulfate was added to 50% saturation, whereby human epidermal growth factor was precipitated. The amount of human epidermal growth factor thus obtained was 26.5 $\mu$g, the purity thereof based on total protein was 0.41%, and the rate of recovery was 88.3%. No placental gonadotropic hormone activity was detected in 1 mg of the protein.

[Notes]

The determination of human epidermal growth factor activity was carried out in accordance with the radioreceptor-assay method of S. Cohen, G. Carpenter: Proc. Nat. Acad. Sci., USA 72, 1317 (1975). The standard m-EGF and $^{125}$I-m-EGF used in the assay were prepared by the method of Carpenter et al. (G. Carpenter, S. Cohen et al.: J. Biol. Chem. 250, 4297 (1975).

The determination of protein was carried out in accordance with Lowry-Folin's method [O. H. Lowry, N. J. Rowelrough, et al.: J. Biol. Chem. 198, 265 (1951)] using bovine serum albumin as a standard.

The determination of human placental gonadotropic hormone activity was carried out using UCG Titration Set (Carter-Wallace Inc., N.J., USA).

The determination of protease activity was carried out in accordance with the method of McDonald [C. E. McDonald and L. L. Chen: Anal. Biochem. 10, 175 (1965)].

We claim:

1. In a method of producing a human epidermal growth factor from human urine wherein said urine is contacted with a hydrous aluminum silicate and wherein said epidermal growth factor is adsorbed on said hydrous aluminum silicate and subsequently eluted therefrom with an alkaline solution, the improvement which comprises the steps of:
   (a) pretreating said urine to precipitate impurities by adjusting the pH to about 8–9 and separating said impurities,
   (b) adding particles of an aluminum or magnesium silicate of the formula:

$$Z.2(\text{or } 6)SiO_2 xH_2O$$

wherein Z is $Al_2O_3$ or $2MgO$; x is the number of water molecules in each molecule of the compound as governed by the water content of the compound, to said urine under neutral to acid conditions to thereby adsorb said factor on said particles and,
   (c) eluting said factor from said particles with an alkaline solution.

2. A method as set forth in claim 1 wherein the aluminiumsilicate used for adsorbing the active factor in human urine is represented by the formula: $Al_2O_3.2(\text{or } 6)\text{-}SiO_2.xH_2O$, wherein x is as defined above.

3. A method as set forth in claim 1 wherein the magnesium silicate used for adsorbing the active factor in human urine is a compound of the formula:

$$2MgO.6SiO_2.xH_2O.$$

wherein x is as defined above.

4. The method of claim 1 wherein said factor is eluted from said particles at a pH of 10–12.

5. A method as set forth in claim 1 wherein said human urine has been previously purified by adding particles of aluminiumsilicate of the formula: $Al_2O_3.9SiO_2.xH_2O$, wherein x is as defined above, silicic acid or aluminum hydroxide to fresh human urine to thereby adsorb impurities on said particles and removing the particles.

6. A method as set forth in claim 5 wherein impurities in human urine are adsorbed by adding to the urine an aluminiumsilicate of the formula: $Al_2O_3.9SiO_2.xH_2O$ under weakly acidic conditions and at a pH 3 to 5, or a silicic acid under weakly acidic conditions at a pH 4 to 6, or aluminum hydroxide under neutral conditions.

7. A method as set forth in claim 5 wherein said silicic acid is represented by the formula $ySiO_2.xH_2O$, wherein x is as defined above; y is the number of silicon oxide molecules in each molecule of the compound.

8. A method as set forth in claim 5 wherein said aluminum hydroxide is represented by the formula $Al_2(OH)_3$.

* * * * *